US010195124B2

(12) United States Patent
Prencipe et al.

(10) Patent No.: US 10,195,124 B2
(45) Date of Patent: Feb. 5, 2019

(54) ORAL CARE COMPOSITION

(71) Applicant: Colgate-Palmolive Company, Piscataway, NJ (US)

(72) Inventors: Michael Prencipe, Princeton Junction, NJ (US); Xiao Yi Huang, Guangzhou (CN); Yuan Hui Xie, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 3 days.

(21) Appl. No.: 14/654,512

(22) PCT Filed: Dec. 24, 2012

(86) PCT No.: PCT/CN2012/087272
§ 371 (c)(1),
(2) Date: Jun. 19, 2015

(87) PCT Pub. No.: WO2014/100930
PCT Pub. Date: Jul. 3, 2014

(65) Prior Publication Data
US 2015/0335539 A1    Nov. 26, 2015

(51) Int. Cl.
*A61K 8/27* (2006.01)
*A61Q 11/00* (2006.01)
*A61K 31/32* (2006.01)
*A61K 8/24* (2006.01)
*A61K 8/19* (2006.01)
*A61K 8/365* (2006.01)
*A61K 8/21* (2006.01)

(52) U.S. Cl.
CPC .................. *A61K 8/24* (2013.01); *A61K 8/19* (2013.01); *A61K 8/21* (2013.01); *A61K 8/27* (2013.01); *A61K 8/365* (2013.01); *A61Q 11/00* (2013.01); *A61K 2800/30* (2013.01)

(58) Field of Classification Search
CPC . A61K 8/27; A61K 8/19; A61K 8/365; A61K 8/21; A61K 8/24; A61K 2800/30; A61Q 11/00
See application file for complete search history.

(56) References Cited

U.S. PATENT DOCUMENTS

| 3,282,792 | A | | 11/1966 | Fiscella |
| 4,335,102 | A | * | 6/1982 | Nakashima ............... A61K 8/19 424/48 |
| 4,363,794 | A | | 12/1982 | Ochiai et al. |
| 5,094,842 | A | * | 3/1992 | Riley ....................... A61K 8/19 424/49 |
| 5,348,733 | A | | 9/1994 | Morishima et al. |
| 6,342,205 | B1 | | 1/2002 | Niemi et al. |
| 2009/0136432 | A1 | | 5/2009 | Strand et al. |
| 2011/0239736 | A1 | * | 10/2011 | Ramji ...................... A61K 8/33 73/23.34 |

FOREIGN PATENT DOCUMENTS

| GB | 1018665 | 1/1966 |
| GB | 1160640 | 8/1969 |
| WO | WO0168046 | 9/2001 |
| WO | WO 2006/069210 A2 | 6/2006 |
| WO | WO2007062365 | 5/2007 |
| WO | WO 2007/076001 | 7/2007 |
| WO | WO2008041055 | 4/2008 |
| WO | WO2009060385 | 5/2009 |
| WO | WO-2014088575 A1 * | 6/2014 ............... A61K 8/27 |

OTHER PUBLICATIONS

International Search Report and Written Opinion for International Application No. PCT/CN2012/087272 dated Sep. 26, 2013.

* cited by examiner

*Primary Examiner* — Lezah Roberts

(57) ABSTRACT

The present invention relates to an oral care composition with a high water content which has improved robustness towards microbial challenge. The oral care composition includes compositions comprising from 0.125 wt % to 0.75 wt % of a water soluble source of stannous ions, wherein the composition comprises at least 50 wt % water and wherein the source of stannous ions is selected from the group consisting of stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof.

8 Claims, No Drawings

ORAL CARE COMPOSITION

BACKGROUND OF THE INVENTION

Compositions having a high water content tend to support the survival and growth of microorganisms. This problem also occurs in oral care compositions which have a high water content. Therefore, preservative agents such as benzyl alcohol, methylparaben, propylparaben are often added to oral care compositions in order to increase their robustness towards microbial challenge.

However, a need still exists for oral care compositions which have improved robustness towards microbial attack without requiring the presence of preservative agents in the compositions.

SUMMARY OF THE INVENTION

A first aspect of the present invention provides an aqueous oral care composition comprising from 0.125 wt % to 0.75 wt % of a water soluble source of stannous ions, wherein the composition comprises at least 50 wt % water and wherein the source of stannous ions is selected from the group consisting of stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof.

Optionally, the composition comprises from 0.125 wt % to 0.75 wt % of the source of stannous ions.

Optionally, the composition comprises from 0.125 wt % to 0.5 wt % of the source of stannous ions.

Optionally, the composition comprises from 0.125 wt % to 0.35 wt % of the source of stannous ions.

Optionally, the composition comprises from 0.15 wt % to 0.3 wt % of the source of stannous ions.

Optionally, the source of stannous ions is stannous chloride.

Optionally, the composition comprises from 50 wt % to 65 wt % water.

Optionally, the composition comprises from 52 wt % to 60 wt % water.

Optionally, the composition comprises from 54 wt % to 55 wt % water

Optionally, the composition further comprises a fluoride ion source selected from the group consisting of sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof.

Optionally, the composition further comprises a source of zinc ions.

Optionally, the source of zinc ions comprises zinc oxide, zinc citrate, or mixtures thereof.

Optionally, the composition comprises zinc citrate in an amount of from 0% to 1.5%, preferably, 1.5 wt % to 2.5 wt %.

Optionally, the composition comprises zinc oxide in an amount of from 0% to 1.5%, preferably 0.5 wt % to 1.5 wt %.

Optionally, the composition is a toothpaste, a tooth gel, a mouthrinse, a cream or an ointment.

Optionally, the composition is free of additional preservative agents.

The present invention also provides an oral care composition as described above which has improved robustness towards microbial challenge.

In a second aspect, the present invention provides use of a water soluble source of stannous ions for improving the robustness towards microbial challenge of an oral care composition containing at least 50 wt % water, wherein the source of stannous ions is present in the oral care composition at a concentration of from 0.1 wt % to 0.75 wt %, and wherein the source of stannous ions is selected from the group consisting of stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof.

Optionally, the composition comprises from 0.15 wt % to 0.3 wt % of the source of stannous ions.

Optionally, the source of stannous ions is stannous chloride.

Optionally, the composition comprises from 50 wt % to 60 wt % water.

The present inventors have surprisingly found that the addition of a stannous ion source at a concentration of 0.1 wt % to 0.75 wt % to a high water content aqueous oral care composition (at least 50 wt % water content) greatly improves the robustness of the composition towards microbial challenge, compared to compositions which do not contain a source of stannous ions or any other chemical reagents that are responsible for preservation.

DESCRIPTION OF THE INVENTION

It should be understood that the detailed description and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition unless otherwise indicated. As referred to herein, "ppm" (parts per million) refers to ppm by weight, unless otherwise indicated. As referred to herein, all ratios refer to weight ratios, unless otherwise indicated.

In one aspect, the present invention provides an aqueous oral care composition comprising from about 0.125 wt % to about 0.75 wt % of a water soluble source of stannous ions, wherein the composition comprises at least 50 wt % water and wherein the source of stannous ions is selected from the group consisting of stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof. Alternatively, the amount of stannous ions throughout the application can be referred to directly, e.g. about 0.125 wt % to about 0.75 wt % of stannous chloride ($SnCl_2$) would correlate to about 0.080 wt % to about 0.47 wt % of stannous ions.

In some embodiments, the composition comprises from about 0.15 wt % to about 0.75 wt % of the source of stannous ions, optionally from about 0.15 wt % to about 0.5 wt % of the source of stannous ions.

In some embodiments, the composition comprises from 0.15 wt % to 0.3 wt % of the source of stannous ions, optionally from 0.20 wt % to 0.25 wt % of the source of stannous ions.

In some embodiments, the composition comprises from 0.3 wt % to 0.5 wt % of the source of stannous ions, optionally 0.35 wt % to 0.45 wt % of the source of stannous ions.

In some embodiments, the source of stannous ions is stannous chloride ($SnCl_2$).

The oral care compositions of the present invention are aqueous, and comprise at least 50 wt % water. In some embodiments, the oral care composition comprises from 50 wt % to 65 wt % water, optionally from 52 wt % to 60 wt % water, further optionally from 54 wt % to 55 wt % water. In some embodiments, the oral care composition comprises from 50 wt % to 60 wt % water.

In some embodiments, the oral care compositions of the present invention further comprise a fluoride ion source selected from the group consisting of sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof. One example of an amine fluoride is Olaflur (N'-octadecyltrimethylendiamine-N,N,N'-tris(2-ethanol)-dihydrofluoride).

In certain embodiments the fluoride ion source includes sodium fluoride, amine fluorides, sodium monofluorophosphate, as well as mixtures thereof. A preferred fluoride salt may be sodium monofluorophosphate.

In certain embodiments, the oral care composition of the invention may contain a fluoride ion source or fluorine-providing ingredient in an amount sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt % to about 10 wt %, e.g., from about 0.003 wt % to about 5 wt %, 0.01 wt % to about 1 wt, or about 0.05 wt %. However, it is to be understood that the weights of fluoride salts to provide the appropriate level of fluoride ion will obviously vary based on the weight of the counter ion in the salt, and one of skill in the art may readily determine such amounts.

In some embodiments, the oral care compositions of the present invention further comprise a source of zinc ions. One or more such sources can be present. One or more zinc ion sources may be present in a total amount of from about 0.05 wt % to about 3 wt %, for example from about 0.1 wt % to about 1 wt %, by total weight of the composition.

Suitable zinc ion sources include without limitation zinc acetate, zinc citrate, zinc gluconate, zinc glycinate, zinc oxide, zinc sulfate, sodium zinc citrate and mixtures thereof.

In certain embodiments, the source of zinc ions comprises zinc oxide (ZnO), zinc citrate, or mixtures thereof. In some embodiments, the composition comprises zinc citrate in an amount of from 1.5 wt % to 2.5 wt %, optionally in an amount of from 1.75 wt % to 2.25 wt %. Alternatively or additionally, the composition may comprise zinc oxide in an amount of from 0.5 wt % to 1.5 wt %, optionally in an amount of from 0.75 wt % to 1.25 wt %.

In some embodiments, the oral care compositions of the present invention may comprise one or more agents selected from abrasives, diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

In some embodiments, the compositions of the present invention further comprise at least one abrasive.

Abrasive silicas are distinct from thickening silicas. In general, abrasive (cleaning) silicas can be characterized as having oil absorption levels of about 40 to 150 cc/100 g and having an Einlehner abrasion of 3 or greater mg loss/100,000 revolutions whereas thickening abrasives have oil absorption levels of greater than 150 cc/100 g and having an Einlehner abrasion of less than 2 mg loss/100,000 revolutions.

Abrasives that may be used include silica abrasives such as precipitated or hydrated silicas having a mean particle size of up to about 20 microns, such as Zeodent 103, 105, 113, 114, 115, or 124 marketed by J. M. Huber Chemicals Division, Havre de Grace, Md. 21078, Sylodent 783 marketed by Davison Chemical Division of W.R. Grace & Company, Sorbosil AC 43 from PQ Corporation, and mixtures thereof. Other useful dentifrice abrasives include aluminium oxide, aluminum silicate, calcined alumina, bentonite or other siliceous materials, insoluble phosphates, calcium carbonate, and mixtures thereof.

Other possible abrasive silicas include silica gels and precipitated amorphous silica having an oil adsorption value of less than 100 cc/100 g silica and optionally in the range of from about 45 cc/100 g to less than about 70 cc/100 g silica. These silicas are colloidal particles having an average particle size ranging from about 3 microns to about 12 microns, and optionally between about 5 to about 10 microns.

The abrasive or mixture of abrasives may be present in an amount of from 5 to 35 wt % based on the weight of the composition, optionally from 10 to 20 wt % based on the weight of the composition. The abrasive or mixture of abrasives may be present in an amount of from 12 to 17 wt % based on the weight of the composition.

In certain embodiments, the compositions may be free of abrasives.

In some embodiments, the oral care compositions of the present invention comprise at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of about 0.1 wt % to about 50 wt %, for example about 0.5 wt % to 20 wt % or 1 wt % to 10 wt %, by total weight of the composition.

In some embodiments, the compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment, the compositions of the invention comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate (SLS), sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt % to about 10 wt %, for example, from about 0.05 wt % to about 5 wt %, or from about 0.1 wt % to about 2 wt % by total weight of the composition.

In some embodiments, the compositions of the invention comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt % to about 10 wt %, for example from about 0.2 wt % to about 5 wt %, or from about 0.25 wt % to about 2 wt %, by total weight of the composition.

In some embodiments, the compositions of the present invention comprise at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly ι-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof.

Silica thickeners such as Zeodent 115 and Zeodent 165 (both available from Huber Engineered Materials) and DT 267 (available from PPG Industries or OSC—Lianji Chemical Industry Co., Ltd.) may also be used. One or more thickening agents are optionally present in a total amount of from about 0.01 wt % to 15 wt %, for example from about 0.1 wt % to about 10 wt %, or from about 0.2 wt % to about 5 wt %, by total weight of the composition.

In some embodiments, the compositions of the invention comprise at least one viscosity modifier, useful for example to help inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt % to about 10 wt %, for example, from about 0.1 wt % to about 5 wt %, by total weight of the composition.

In some embodiments, the compositions of the invention comprise at least one humectant. Any orally acceptable humectant can be used, including without limitation, polyhydric alcohols such as glycerine, sorbitol (particularly as a 70% solution), xylitol or low molecular weight polyethylene glycols (PEGs) such as PEG 600. Many humectants also function as sweeteners. One or more humectants are optionally present in a total amount of from about 1 wt % to about 70 wt %, for example, from about 1 wt % to about 50 wt %, from about 2 wt % to about 25 wt %, or from about 5 wt % to about 15 wt %, by total weight of the composition.

In some embodiments, a composition of the present invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (such as sodium saccharin), dipeptide-based intense sweeteners, cyclamates and the like. One or more sweeteners are optionally present in a total amount depending strongly on the particular sweetener(s) selected, but typically 0.005 wt % to 5 wt %, by total weight of the composition, optionally 0.005 wt % to 0.3 wt %, fluffier optionally 0.05 wt % to 0.1 wt % by total weight of the composition.

In some embodiments, a composition of the present invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., and other flavors, adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt % to about 5 wt %, for example, from about 0.03 wt % to about 2.5 wt %, optionally about 0.05 wt % to about 1.5 wt %, further optionally about 0.1 wt % to about 0.3 wt % by total weight of the composition.

A composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide ($TiO_2$), zinc oxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt % to about 20 wt %, for example, from about 0.01 wt % to about 10 wt %, or from about 0.1 wt % to about 5 wt %, by total weight of the composition.

The compositions of the present invention optionally comprise an antibacterial agent such as chlorhexicline, triclosan, quaternary ammonium compounds (for example benzalkonium chloride) or an additional preservative agent such as parabens (for example methylparaben or propylparaben). One or more antibacterial or preservative agent is optionally present in the composition in a total amount of from about 0.01 wt % to about 0.5 wt %, optionally about 0.05 wt % to about 0.1 wt % by total weight of the composition.

In some embodiments, the composition is free of such additional antibacterial or preservative agents.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt % to about 20 wt % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-cliphosphonic acid), N-methyl azacyclopentane-2,3-diphosphonic acid, ethane-1-hydroxy-1,1-cliphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, monosodium pyrophosphate, disodium pyrophosphate, trisodium pyrophosphate, tetrasodium pyrophosphate (TSPP), tetrapotassium pyrophosphate (TKPP), sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

Embodiments of the present invention are further described in the following examples. The examples are merely illustrative and do not in any way limit the scope of the invention as described and claimed.

EXAMPLES

Compositions A to G were formulated, as shown in Table 1, in order to assess the impact of different concentrations of $SnCl_2$ on the robustness of a high water-content silica-based dentifrice against microbial challenge. Each of these compositions has a high total water content (from both CP water and from the 70% sorbitol solution).

The Micro Robustness Index (MRI) of each of these compositions was measured. The Micro Robustness Index is used as a quantitative measure of a composition's ability to withstand microbial challenge. The MRI is the result from a challenge test assessing the antimicrobial efficacy of a compound/composition against a pool of microorganisms including *Burkholderia cepacia, Enterobacter cloacae, Escherichia coil, Klesiella oxytoca, Klebsiella pneumoniae, Serratia marcescens, Providencia rettgeri, Pseudomonas aeruginosa, Pseudomonas putida, Staphylococcus aureus, Staphylococcus saprophyticus*. Samples are challenged 3 times at 30 minute intervals with an innoculum of $10^7$ bacteria from the above listed pool. After 4, 6 and 24 hours, aliquots are tested to measure the log reduction of bacteria. Using these data, the area under the curve (AUC) is calculated and then converted into the MRI; the higher the MRI, the greater the microrobustness of the tested composition.

The present inventors have found that an MRI of at least 0.75 is required in order to show that a composition has an acceptable level of robustness against microbial attack. MRI lower than 0.75 may not adequately reduce the pool of microorganisms and results in greater risk of microbial attack.

The Micro Robustness Index (MRI) for each of Compositions A to F are shown in Table 1 (all figures are in percent by weight).

TABLE 1

|  | A | B | C | D | E | F | G | H |
|---|---|---|---|---|---|---|---|---|
| Water | 48.00 | 48.05 | 48.00 | 47.95 | 45.45 | 47.80 | 47.60 | 47.35 |
| sorbitol-70% solution | 22.44 | 22.00 | 22.00 | 22.00 | 22.00 | 22.00 | 22.00 | 22.00 |
| Polyethylene Glycol 600 | 2.00 | 2.00 | 2.00 | 2.00 | 2.00 | 2.00 | 2.00 | 2.00 |
| sodium saccharin | 0.30 | 0.30 | 0.30 | 0.30 | 0.30 | 0.30 | 0.30 | 0.30 |
| AC 43 | 5.00 | 5.00 | 5.00 | 5.00 | 5.00 | 5.00 | 5.00 | 5.00 |
| ZnO | — | — | — | — | 1.00 | — | — | — |
| Zinc Citrate | 2.00 | 2.00 | 2.00 | 2.00 | — | 2.00 | 2.00 | 2.00 |
| TSPP | 0.50 | 0.50 | 0.50 | 0.50 | 1.00 | 0.50 | 0.50 | 0.50 |
| TKPP | — | — | — | — | 2.00 | — | — | — |
| sodium bicarbonate | — | — | — | — | 1.00 | — | — | — |
| $SnCl_2$ | 0.00 | 0.05 | 0.10 | 0.15 | 0.15 | 0.30 | 0.50 | 0.75 |
| CMC | 1.00 | 1.00 | 1.00 | 1.00 | 1.00 | 1.00 | 1.00 | 1.00 |
| Xanthan | 0.30 | 0.30 | 0.30 | 0.30 | 0.30 | 0.30 | 0.30 | 0.30 |
| MFP | 0.76 | 1.10 | 1.10 | 1.10 | 1.10 | 1.10 | 1.10 | 1.10 |
| Silica abrasive | 10.00 | 10.00 | 10.00 | 10.00 | 10.00 | 10.00 | 10.00 | 10.00 |
| Silica thickener | 4.00 | 4.00 | 4.00 | 4.00 | 4.00 | 4.00 | 4.00 | 4.00 |
| Sodium lauryl sulfate powder | 2.00 | 2.00 | 2.00 | 2.00 | 2.00 | 2.00 | 2.00 | 2.00 |
| Flavorant | 1.20 | 1.20 | 1.20 | 1.20 | 1.20 | 1.20 | 1.20 | 1.20 |
| $TiO_2$ | 0.50 | 0.50 | 0.50 | 0.50 | 0.50 | 0.50 | 0.50 | 0.50 |
| TOTAL | 100.00 | 100.00 | 100.00 | 100.00 | 100.00 | 100.00 | 100.00 | 100.00 |
| MRI | 0.29 | 0.31 | 0.34 | 0.76 | 0.83 | 0.91 | 0.91 | 1.02 |
| Total water content | 57.73 | 54.65 | 54.60 | 54.55 | 52.05 | 54.40 | 54.20 | 53.95 |

As shown in Table 1, Compositions A-C (which contained less than 0.125 wt % $SnCl_2$) had unacceptable MRI. This composition therefore did not have an acceptable level of robustness towards microbial challenge.

However, it can be seen from the results in Table 1 that the high water content compositions which contained between 0.15 wt % and 0.75 wt % $SnCl_2$ gave MRI values of greater than 0.75. These compositions therefore show an acceptable level of robustness towards microbial challenge. While a concentration of 0.15 wt % $SnCl_2$ allowed the composition to attain the MRI>0.75 acceptance criteria, a concentration of 0.3 wt % $SnCl_2$ allowed the composition to attain an excellent result of MRI=0.91. In contrast, compositions up to 0.10 wt % $SnCl_2$ showed insufficient MRI, not even reaching half the 0.75 target.

While additional $SnCl_2$ could be added, the increase in MRI was relatively negligible compared to the cost of a 66% increase in $SnCl_2$ (0.3 wt % vs. 0.5 wt %) or a 150% increase in $SnCl_2$ (0.3 wt.% vs. 0.75 wt %). Moreover, $SnCl_2$ is an astringent compound that tastes even worse than $SnF_2$ (which has a bitter, salty taste) and one of skill in the art would be motivated to minimize the amount used once a requisite level of MRI has been achieved.

Whilst particular embodiments of the invention have been illustrated and described, it will be obvious to those skilled in the art that various changes and modifications may be made without departing from the scope of the invention as defined in the appended claims.

The invention claimed is:

1. An aqueous oral care composition comprising from 0.15 wt % to 0.3 wt % of a water soluble source of stannous ions, wherein the composition comprises from 52 wt % to 60 wt % water and wherein the source of stannous ions is stannous chloride; wherein the composition has a pH from 7 to 9;

wherein the composition further comprises a source of zinc ions comprising zinc citrate in an amount of from 2.0 wt % to 2.5 wt % and wherein the composition further comprises tetrasodium pyrophosphate (TSPP).

2. The oral care composition of claim 1, wherein the composition comprises from 54 wt % to 55 wt % water.

3. The oral care composition of claim 1, further comprising a fluoride ion source selected from the group consisting of sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof.

4. The oral care composition of claim 1, wherein the composition further comprises zinc oxide in an amount of from 0.5 wt % to 1.5 wt %.

5. The oral care composition of claim 1, wherein the composition is a toothpaste, a tooth gel, a mouthrinse, a cream or an ointment.

6. The oral care composition of claim 1, wherein the composition is free of additional antibacterial or preservative agents.

7. The oral care composition of claim 1, wherein the composition has improved robustness towards microbial challenge.

8. A method of improving the robustness of an oral care composition containing 52 wt % to 60 wt % water towards microbial challenge comprising adding to the oral care composition a water soluble source of stannous ions, wherein the source of stannous ions is present in the oral care composition at a concentration of from 0.15 wt % to 0.3 wt %, and wherein the source of stannous ions is stannous chloride; wherein the composition has a pH from 7 to 9;

and wherein the composition further comprises a source of zinc ions comprising zinc citrate in an amount of from 2.0 wt % to 2.5 wt % and wherein the composition further comprises tetrasodium pyrophosphate (TSPP).

* * * * *